United States Patent [19]

Schumann

[11] Patent Number: 4,636,089

[45] Date of Patent: Jan. 13, 1987

[54] PROCESS AND APPARATUS FOR THE QUENCHING INTENSITY OF LIQUID QUENCHING BATCHS

[75] Inventor: Erwin Schumann, Bruchkobel, Fed. Rep. of Germany

[73] Assignee: DeGussa Aktiengesellschaft, Frankfurt am Main, Fed. Rep. of Germany

[21] Appl. No.: 612,804

[22] Filed: May 22, 1984

[30] Foreign Application Priority Data

Jun. 3, 1983 [DE] Fed. Rep. of Germany ....... 3320055

[51] Int. Cl.$^4$ ............................................. G01N 25/00
[52] U.S. Cl. ........................................ 374/45; 374/43
[58] Field of Search ................. 374/45, 43, 44; 73/53; 148/6.14 A; 266/120

[56] References Cited

U.S. PATENT DOCUMENTS

| | | | |
|---|---|---|---|
| 2,587,622 | 3/1952 | Jaffe | 374/43 |
| 3,045,473 | 7/1962 | Hager, Jr. | 374/44 |
| 3,822,580 | 7/1974 | Jamet et al. | 374/43 |
| 4,412,752 | 11/1983 | Cellitti et al. | 374/43 |
| 4,487,398 | 12/1984 | Lincoln et al. | 266/120 |

*Primary Examiner*—Charles Frankfort
*Assistant Examiner*—W. Morris Worth
*Attorney, Agent, or Firm*—Cushman, Darby & Cushman

[57] ABSTRACT

There is obtained a continuous rapidly responding and controllable measurement of the quenching intensity of quenching baths. A test body is inserted into the bath and a controlled heating is applied to a portion of the surface of the test body raising the temperature of that portion of the test body surface to a constant temperature of 50° to 700° C., especially 150° to 400° C. higher than the temperature of the bath. The heat energy required to maintain this temperature constant is used as a measure of the quenching intensity of the bath.

13 Claims, 1 Drawing Figure

PROCESS AND APPARATUS FOR THE QUENCHING INTENSITY OF LIQUID QUENCHING BATCHS

BACKGROUND OF THE INVENTION

The invention is directed to a process and an apparatus for measuring the quenching intensity of liquid quenching baths, especially salt baths by introducing into the bath a test body which has been heated to a temperature higher than the bath temperature.

The quenching after austenitization in the heat treatment of steels represents an important step in the termination of the process. The liquid baths such as oil or water baths used for this purpose thereby can have various quenching rates, effectiveness, or intensities depending on their temperature, composition, movement of the bath, and possible sludge. Above all, this is true for the so-called heating bath, a salt melt made of alkali nitrates and nitrites.

Besides the motion of the bath and the sludge content, a decisive condition is played by the water content of the salt melt. A water content of 1% can increase the quenching intensity, e.g. to double the amount.

Therefore the testing of the quenching intensity of these baths is indispensable in order to produce the necessary hardness results in the heat treatment of steels. Previously the methods of testing depended essentially on copying the quenching process. A test body was heated to hardening temperature and then cooled in the quenching bath, in which case the cooling time was measured for a fixed temperature interval. the test bodies can be constructed either with very poor heat capacity and very good heat conductivity as silver balls or can be present as massive steel bodies which react very slowly to the quenching. This test method is very cumbersome and practically unusable for continuous supervision of the quenching intensity of the baths if it is a question of obtaining an immediate test result for a controller which should influence the quenching intensity, e.g. by addition of water.

Therefore it is the object of the present invention to provide a process and apparatus for measuring the quenching intensity of liquid quenching baths, especially salt baths by inserting into the bath a test body heated to a temperature above the bath temperature whereby the measurement device reacts quickly, is suited to a continuous supervision, and should yield a controlled signal representing the measured value.

SUMMARY OF THE INVENTION

These objects are solved according to the invention by means of applying a controllable heating to a portion of the surface of the test body surface and thereby raising its temperature to a constant higher temperature which is 50° to 700° C. higher than that of the bath and using the heat energy required to maintain the temperature constant as a measure of the quenching intensity or effectiveness.

Preferably the excess temperature of the partial surface compared to the bath temperature is 150° to 400° C. in which case it has proven advantageous to apply the excess temperature to a partial area of a size of 0.1 to 10 cm$^2$, especially 1 to 6 cm$^2$. Furthermore, it is advantageous for continuous measurement if the heated portion of the surface is located on a level surface of the test body and this is securely arranged on a slope in the bath.

According to the process of the invention the quenching intensity of the liquid bath is ascertained by means of the test body which has a "hot spot" having a temperature which is held constant, which temperature is higher than the temperature of the bath, whereby the energy necessary to maintain the excess temperature of the "hot spot" furnishes a measure for the quenching intensity of the bath. In this way there is obtained a very quickly available controlled signal which is best suited for a continuous supervision and control of the quenching intensity of the bath.

This process is preferably carried out with a test body which has an impervious housing resistant to the bath liquid, whereby there is arranged inside the housing in heat insulated manner, a controlled, heated heat transfer body which is connected in heat conducting manner via its front surface with the test body housing.

Preferably the heat transfer body is provided with a plug of small cross section whose front surface accomplishes the heat transfer to the test body housing and produces the "hot spot". It is also advantageous if the controlled heating to maintain the excess temperature of the "hot spot" is provided for within the heat transfer body. The size of the front surface of the heat transfer body or the plug and therewith the "hot spot" is preferably in the range of 0.1 to 10 cm$^2$, especially in the range of 1 to 6 cm$^2$.

The process can comprise, consist essentially of, or consist of the recited steps.

BRIEF DESCRIPTION OF THE DRAWING

The single view of the drawing is a longitudinal section through an illustrative test body.

DETAILED DESCRIPTION

Figure 1:
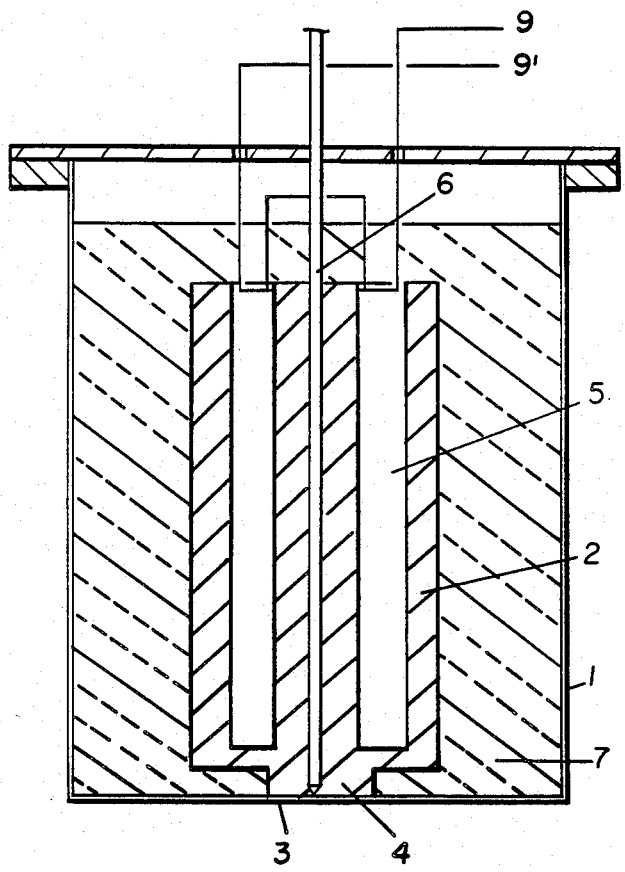

The heat transfer body 2 consisting of a metal preferably having a very high thermal conductivity (Cu or Ag) with the front surface 3 of the plug 4 rests on the wall of the test body housing 1. The advantageously thin sheet (about 0.5 mm) of the test body housing 1 is of low heat conductivity (e.g. Cr-Ni-steel) and is joined with the front surface 3 of the plug 4 in good heat conducting manner, e.g. by solders. The size of the front surface 3 of the plug 4 forms the "hot spot". The heat transfer body 2 is accomodated with heat insulation in the test body housing and is heated for example by controlled electrical resistance hot cartridges 5 or electrical resistance wires connected to lead wires 9 and 9'. The temperature of the "hot spot" 3 is measured by a thermocouple element 6. It should be understood that the heating of the heat transfer body 2 can also be carried out from an external source in which case the heat transfer body is always surrounded by heat insulation 7.

The recording and measuring of the necessary heating power for maintaining the temperature of the "hot spot" can be carried out with known apparatuses. The same is true for the control of the quenching intensity of the baths, while the bath parameters which have an influence on the quenching intensity are influenced correspondingly by deviation from the nominal value.

The substantially larger cross-section of the heat transfer body 2 compared to the plug 4 permits the accomodation of a relatively high thermal capacity in the test body and together with the very good thermal conductivity of the material provides for a low temperature gradient in the heat transfer body 2. The size of the "hot spot" is determined by the cross-section of the plug 4 which functions as a controllable heat transfer body. Since the test body housing 1 advantageously has a low thermal conductivity and thickness, at least in the region of the "hot spot", the heat cannot spread out radially. Almost the entire energy supplied to the heat transfer body therefore is led via the front surface of the plug 4 to the "hot spot" and is given up there to the bath.

For example, there were carried out experiments for measuring the quenching intensity of alkali nitrate baths at 160° C. (e.g. sodium nitrate or potassium nitrate), or sodium nitrite or potassium nitrite baths which have a plug diameter of 20 mm and in which "hot spots" have been placed by means of heating to a temperature of 500° C., i.e., to an excess temperature of 340° C.

What is claimed is:

1. A process for measuring a quenching characteristic of a liquid salt utilizing a heat transfer body of the type having a housing surrounding said heat transfer body, said heat transfer body having a plug portion on a surface thereof with said plug portion having a surface area that is substantially less than the surface area of the heat transfer body, said plug portion being in heat engaging relation with a portion of the housing to thereby define a test hot spot on said housing surface, said housing including insulation means isolating said heat transfer body from said housing except in the area of said plug portion engaging said housing, said process including the steps of inserting the portion of the housing containing at least said plug portion into the bath, applying a controlled heating to said heat transfer body to thereby raise the temperature of the hot spot to a constant higher temperature which is from 50 to 700 degrees C. above that of the bath and measuring the heat energy required to maintain the temperature of the test hot spot constant while heat transfer occurs between said test hot spot and said bath, wherein said heat energy serves as a measurement of the quenching characteristic of the bath.

2. A process according to claim 1 wherein the bath is a salt bath.

3. A process according to claim 2 wherein the salt is sodium nitrate, sodium nitrite, potassium nitrate, or potassium nitrite.

4. A process according to claim 1 wherein the constant higher temperature is 150° to 400° C. above that of the bath.

5. A process according to claim 4 wherein the hot spot has an area of 0.1 to 10 cm$^2$.

6. A process according to claim 1 wherein the hot spot has an area of 0.1 to 10 cm$^2$.

7. A process according to claim 6 wherein the hot spot has an area of 1 to 6 cm$^2$.

8. A process according to claim 5 wherein the hot spot has an area of 1 to 6 cm$^2$.

9. An apparatus for measuring a quenching characteristic of a liquid quenching bath comprising an impervious housing containing a heat transfer body, said housing being resistant to the liquid bath, said apparatus including means for heating said heat transfer body to a pre-selected temperature, said heat transfer body having a plug portion which is in heat transfer engagement with said housing so as to define a hot spot on said housing, said housing including insulation means isolating said heat transfer body from the housing except in the area of said hot spot, said plug portion having a housing engaging surface area that is substantially less than the surface area of said housing and substantially less than the surface area of the rest of said heat transfer body, said apparatus including means for determining the temperature of said hot spot on said housing, and means for measuring the heat energy required to maintain said hot spot at a preselected temperature, said heat energy serving as a measurement of the quenching characteristic of the bath.

10. An apparatus according to claim 9 including controllable heating means within the heat transfer body.

11. An apparatus according to claim 9 including controllable heating means within the heat transfer body.

12. The apparatus as claimed in claim 9 wherein said plug has a surface in heat transfer relationship with said housing, said surface having a size of 0.1 to 10 cm$^2$.

13. The apparatus as claimed in claim 12 wherein said housing has a surface in contact with said plug, said surface of said housing being made of a material having low heat conductivity.

* * * * *